US011109785B2

(12) United States Patent
Woo et al.

(10) Patent No.: US 11,109,785 B2
(45) Date of Patent: Sep. 7, 2021

(54) FIVE-BEVEL CANNULA FOR BLOOD ACQUISITION DEVICES

(71) Applicant: Becton, Dickinson and Company, Franklin Lakes, NJ (US)

(72) Inventors: Matthew Siang Si Woo, Singapore (SG); Ravi Attri, Budd Lake, NJ (US); Arun U. Nair, Whippany, NJ (US); Bo Yon Lillian Yoo, Ridgefield, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 117 days.

(21) Appl. No.: 15/270,308

(22) Filed: Sep. 20, 2016

(65) Prior Publication Data

US 2017/0086725 A1 Mar. 30, 2017

Related U.S. Application Data

(60) Provisional application No. 62/222,807, filed on Sep. 24, 2015.

(51) Int. Cl.
*A61B 5/15* (2006.01)
*A61M 5/32* (2006.01)

(52) U.S. Cl.
CPC .... *A61B 5/150106* (2013.01); *A61B 5/15003* (2013.01); *A61B 5/150396* (2013.01); *A61M 5/3286* (2013.01)

(58) Field of Classification Search
CPC ........... A61B 5/14; A61B 5/1405; A61B 5/15; A61B 5/150106; A61B 5/15003; A61B 5/150396; A61M 5/42; A61M 5/3286; A61M 5/32
See application file for complete search history.

(56) References Cited

U.S. PATENT DOCUMENTS 145,217 A * 12/1873 Leiter ................ A61M 5/31511
604/218
5,536,259 A 7/1996 Utterberg
5,575,780 A 11/1996 Saito
(Continued)

FOREIGN PATENT DOCUMENTS

AU 766720 B2 9/2001
AU 200197239 2/2002
(Continued)

*Primary Examiner* — Jason M Sims
*Assistant Examiner* — James Stewart Stambaugh, III
(74) *Attorney, Agent, or Firm* — The Webb Law Firm

(57) ABSTRACT

A needle including a cannula having a multi-beveled point is disclosed. The multi-beveled point includes a primary bevel, two middle bevels, and two tip bevels. Each of the middle bevels extends between the primary bevel and one of the tip bevels. The primary bevel is provided on the cannula at a first angle of inclination and a first angle of rotation, the two middle bevels are provided on the cannula at a second angle of inclination and a second angle of rotation, and the two tip bevels are provided on the cannula at a third angle of inclination and a third angle of rotation. The third angle of inclination is greater than the second angle of inclination, the second angle of inclination is greater than the first angle of inclination, and the second angle of rotation is equal to the third angle of rotation.

24 Claims, 7 Drawing Sheets

(56) References Cited

U.S. PATENT DOCUMENTS

| | | |
|---|---|---|
| 5,752,942 A * | 5/1998 | Doyle .................... B24B 19/16 |
| | | 604/274 |
| 6,009,933 A | 1/2000 | Doyle et al. |
| 6,517,523 B1 | 2/2003 | Kaneko et al. |
| 6,629,963 B2 | 10/2003 | Prais et al. |
| 7,252,653 B2 | 8/2007 | Ueda et al. |
| 7,320,683 B2 | 1/2008 | Prais et al. |
| 7,468,055 B2 * | 12/2008 | Prais .................... A61M 5/3202 |
| | | 604/272 |
| 2001/0039402 A1 | 11/2001 | Prais et al. |
| 2002/0111566 A1 * | 8/2002 | Maclean Crawford ...................... |
| | | A61M 25/0631 |
| | | 600/583 |
| 2009/0187153 A1 | 7/2009 | West et al. |
| 2012/0010573 A1 | 1/2012 | Lundquist |
| 2012/0083727 A1 | 4/2012 | Barnett |
| 2013/0218102 A1 * | 8/2013 | Iwase .................... A61M 5/42 |
| | | 604/272 |
| 2013/0226103 A1 | 8/2013 | Papiorek |
| 2014/0305196 A1 | 10/2014 | Ellis et al. |
| 2015/0157359 A1 | 6/2015 | Shinzato et al. |

FOREIGN PATENT DOCUMENTS

| | | |
|---|---|---|
| CN | 200942227 Y | 9/2007 |
| DE | 10207770 A1 | 9/2003 |
| DE | 10224101 A1 | 12/2003 |
| DE | 102005027147 A1 | 12/2006 |
| EP | 2229197 | 9/2010 |
| EP | 2647398 A1 | 10/2013 |
| FR | 2757405 A1 | 6/1998 |
| JP | 200595571 A | 4/2005 |
| JP | 2007159659 A | 6/2007 |
| JP | 2013141488 A | 7/2013 |
| JP | 2015147042 A | 8/2015 |
| RU | 2219960 C2 | 12/2003 |
| RU | 2515147 C2 | 5/2014 |
| WO | 02074367 A2 | 9/2002 |
| WO | 2009091895 A2 | 7/2009 |
| WO | 2014033901 A1 | 3/2014 |
| WO | 2014172239 A1 | 10/2014 |
| WO | 2015126926 A1 | 8/2015 |
| WO | 2013187483 A1 | 2/2016 |

\* cited by examiner

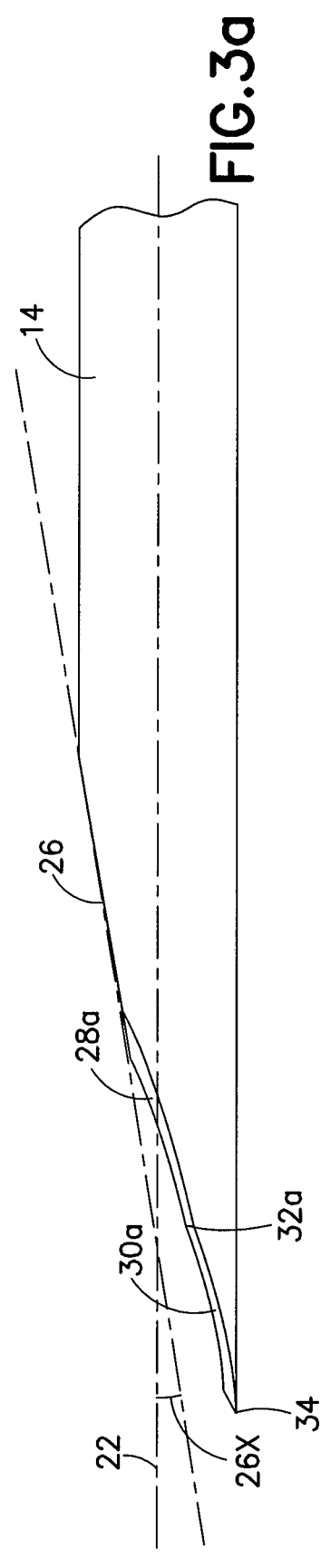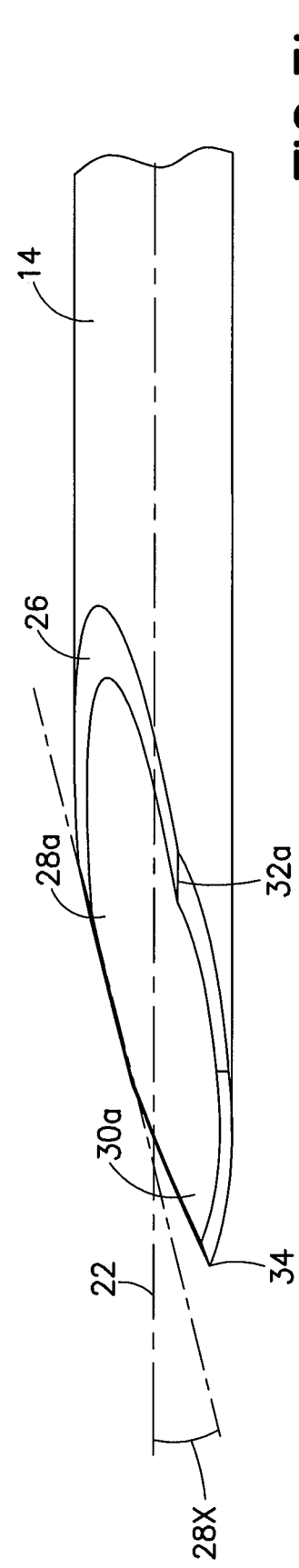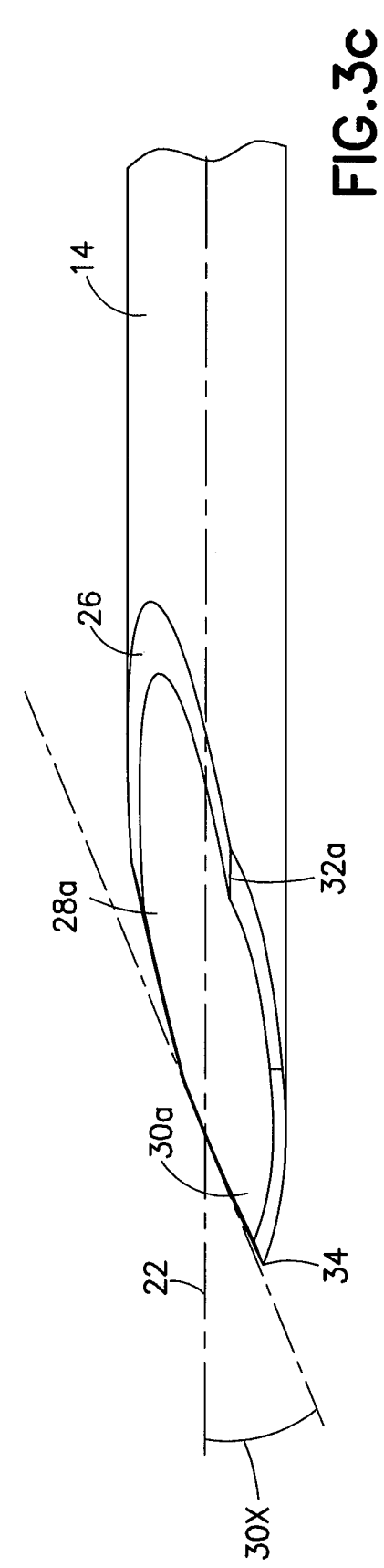

FIVE-BEVEL CANNULA FOR BLOOD ACQUISITION DEVICES

CROSS-REFERENCE TO RELATED APPLICATION

The present application claims priority to U.S. Provisional Application Ser. No. 62/222,807, filed Sep. 24, 2015, entitled "Five-Bevel Cannula for Blood Acquisition Devices", the entire disclosure of which is hereby incorporated by reference.

BACKGROUND OF THE INVENTION

Field of the Invention

The present invention relates to a point geometry for a needle, and more particularly, to a five-beveled point geometry for a needle for reducing needle penetration force.

Description of Related Art

Needles are used in the medical field to obtain samples, such as blood, from patients. Such needles are formed from an elongate tube or cannula having a fluid-conducting lumen and a central axis. The proximal end of the needle is typically configured for mating to, or is otherwise affixed to, a fluid collection device such as a syringe assembly or a blood collection assembly. The distal end of the needle is provided with a pointed tip geometry for piercing a patient's skin or tissue so as to obtain a sample from the patient. A need exists for an improved needle which minimizes patient discomfort and achieves appropriate sample access.

SUMMARY OF THE INVENTION

When designing the pointed tip of the needle, numerous considerations must be taken into account. For instance, it is desirable to minimize the needle penetration force necessary for urging the pointed tip of the needle through the skin and flesh structure of the patient. This force is directly related to the resistance of the cannula point to moving through the skin and the underlying tissue. It is generally recognized that by reducing needle penetration force, the patient will experience less pain, making the sample collection more comfortable. Further, it is believed that the pain experienced by the patient during needle insertion is caused by the cutting of the tissue by the bevel edges at the cannula tip and subsequent stretching of the tissue by the cannula body. The more gradual the transition between the differing bevels of the tip, the smoother the cutting and stretching action of the cannula.

Another consideration in designing point geometry is to prevent or otherwise minimize tissue coring. Coring results when a portion of a material through which the needle has penetrated becomes lodged in the lumen adjacent the pointed tip.

In accordance with an embodiment of the present invention, a needle having a multi-beveled point includes a cannula having a lumen and a central axis defined therethrough, the multi-beveled point provided at one end of the cannula. The multi-beveled point includes a primary bevel, two middle bevels, and two tip bevels, wherein each of the middle bevels extends between the primary bevel and one of the tip bevels. The primary bevel is provided on the cannula at a first angle of inclination with respect to the central axis and a first angle of rotation with respect to the central axis, the two middle bevels are provided on the cannula at a second angle of inclination with respect to the central axis and a second angle of rotation with respect to the central axis, and the two tip bevels are provided on the cannula at a third angle of inclination with respect to the central axis and a third angle of rotation with respect to the central axis. The third angle of inclination is greater than the second angle of inclination and the second angle of inclination is greater than the first angle of inclination, and the second angle of rotation is equal to the third angle of rotation.

In certain embodiments, the first angle of inclination is between 8° and 12°. The first angle of inclination may be 10°. In other embodiments, the second angle of inclination is between 10° and 20°, such as between 15° and 20°. The second angle of inclination may be 15°. In other embodiments, the third angle of inclination is between 18° and 28°, such as between 21° and 28°. The third angle of inclination may be 23°.

The first angle of rotation may be different from the second angle of rotation and the third angle of rotation. The first angle of rotation may be 0°. The second angle of rotation and the third angle of rotation may be between 30° and 50°. Optionally, the second angle of rotation and the third angle of rotation may be between 36° and 50°, such as between 40° and 50°.

In accordance with another embodiment of the present invention, a syringe assembly includes a syringe barrel and a needle attached to the syringe barrel, the needle having a cannula having a lumen and a central axis defined therethrough. The needle includes a multi-beveled point provided at one end of the cannula. The multi-beveled point includes a primary bevel, two middle bevels, and two tip bevels, wherein each of the middle bevels extends between the primary bevel and one of the tip bevels. The primary bevel is provided on the cannula at a first angle of inclination with respect to the central axis and a first angle of rotation with respect to the central axis, the two middle bevels are provided on the cannula at a second angle of inclination with respect to the central axis and a second angle of rotation with respect to the central axis, and the two tip bevels are provided on the cannula at a third angle of inclination with respect to the central axis and a third angle of rotation with respect to the central axis. The third angle of inclination is greater than the second angle of inclination and the second angle of inclination is greater than the first angle of inclination. The second angle of rotation is equal to the third angle of rotation.

In certain embodiments, the first angle of inclination is between 8° and 12°. The second angle of inclination is between 10° and 20°. The third angle of inclination is 18° and 28°. In certain configurations, the first angle of rotation is different from the second angle of rotation and the third angle of rotation. The first angle of rotation may be 0° and the second angle of rotation and the third angle of rotation may be between 30° and 50°.

In accordance with another embodiment of the present invention, a blood collection device includes a hub, and a needle extending from the hub, the needle having a cannula having a lumen and defining a central axis therethrough. The needle having a multi-beveled point provided at one end of the cannula. The multi-beveled point includes a primary bevel, two middle bevels, and two tip bevels. Each of the middle bevels extends between the primary bevel and one of the tip bevels. The primary bevel is provided on the cannula at a first angle of inclination with respect to the central axis and a first angle of rotation with respect to the central axis, the two middle bevels are provided on the cannula at a second angle of inclination with respect to the central axis and a second angle of rotation with respect to the central axis, and the two tip bevels are provided on the cannula at a third angle of inclination with respect to the central axis and a third angle of rotation with respect to the central axis. The third angle of inclination is greater than the second angle of inclination and the second angle of inclination is greater than the first angle of inclination. The second angle of rotation is equal to the third angle of rotation.

In certain configurations, the blood collection device further includes a pair of wings extending transversely from the hub. Optionally the pair of wings is rotatable with respect to the hub. In certain configurations the blood collection device further includes a tube holder connected to the hub for receiving a collection container therein.

In certain configurations, the first angle of inclination may be between 8° and 12°. The second angle of inclination may be between 10° and 20°. The third angle of inclination may be between 18° and 28°. In certain configurations, the first angle of rotation is different from the second angle of rotation and the third angle of rotation. Optionally, the first angle of rotation is 0°, and the second angle of rotation and the third angle of rotation are between 30° and 50°.

BRIEF DESCRIPTION OF THE DRAWINGS

FIG. 3a is a side view of the multi-beveled needle of FIG. 1 showing the angle of inclination of the primary bevel;

FIG. 3b is a side view of the multi-beveled needle of FIG. 1 rotated about the central axis to show the angle of inclination of the middle bevel;

FIG. 3c is a side view of the multi-beveled needle of FIG. 1 rotated about the central axis to show the angle of inclination of the tip bevel;

DETAILED DESCRIPTION OF THE INVENTION

Figure 1:
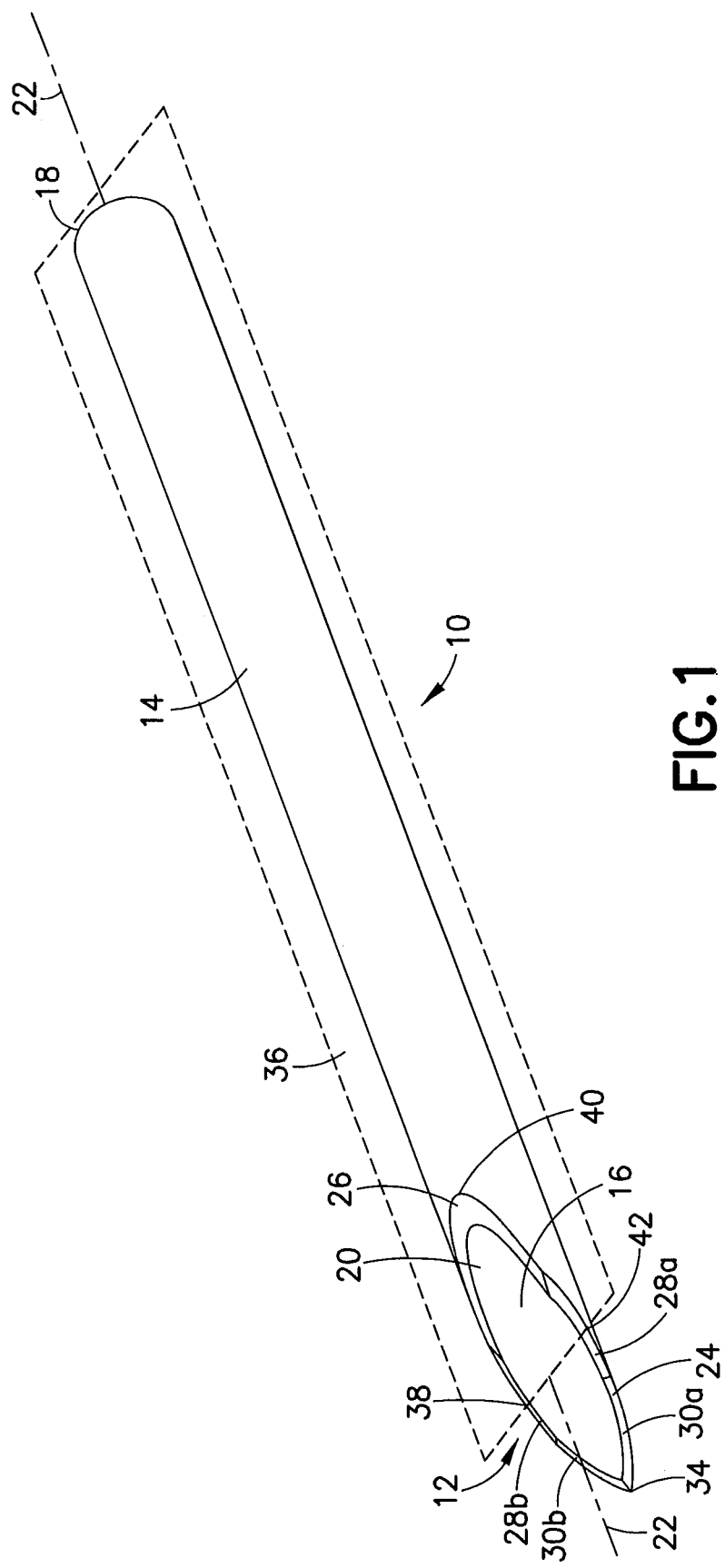
FIG. 1 is a front perspective view of a multi-beveled needle according to the present invention.
Figure 2:
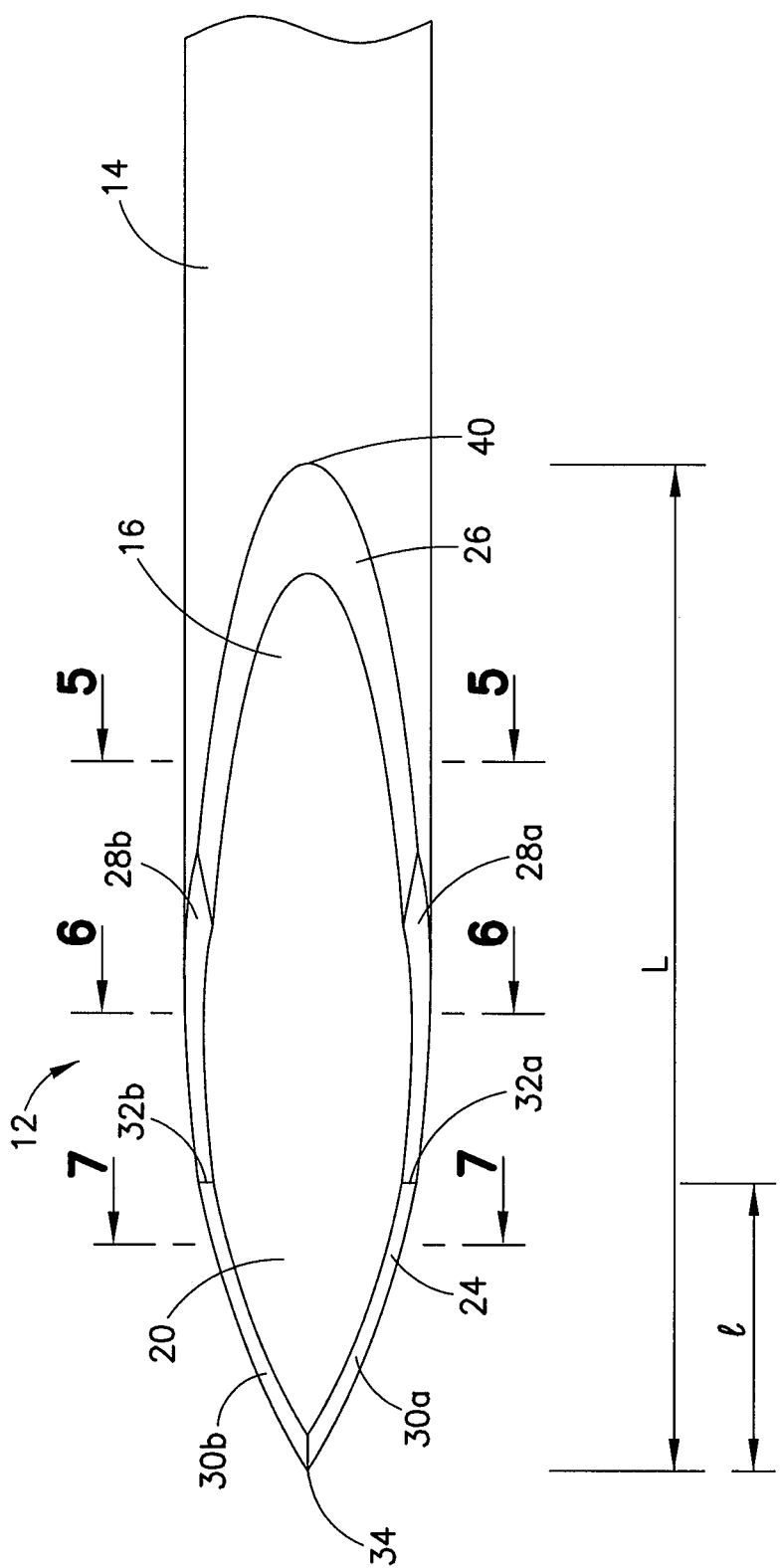
FIG. 2 is a top view of the tip of the multi-beveled needle of FIG. 1.
Figure 4:
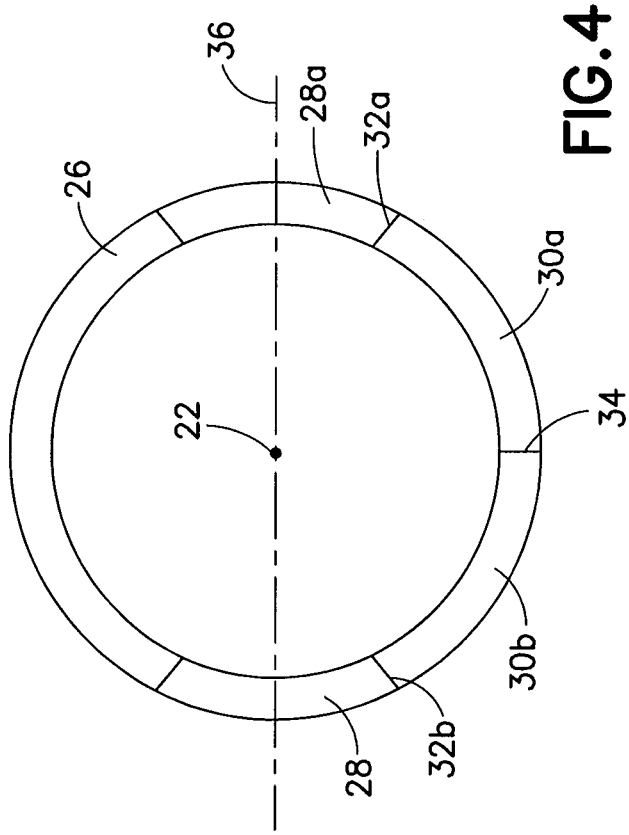
FIG. 4 is a front view of the multi-beveled needle of FIG. 1.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting. It is understood herein that the identified ranges include the outermost bounds of the ranges recited and all numeric valuations therebetween.

As shown in FIGS. 1-3c, the present invention is directed a needle 10 having a multi-beveled point 12. The needle 10 is formed from a tube or cannula 14 defining therein a fluid carrying duct or lumen 16. The needle 10 may be formed of metal, such as medical grade stainless steel and/or medical grade polymeric materials. The needle 10 includes a proximal end 18 which can be secured to a medical delivery instrument 5, such as a syringe assembly 44 (FIG. 8) or a blood collection assembly 46 (FIG. 9), such as the Vacutainer™ push-button blood collection set commercially available from Becton, Dickinson and Company.

Figure 8:
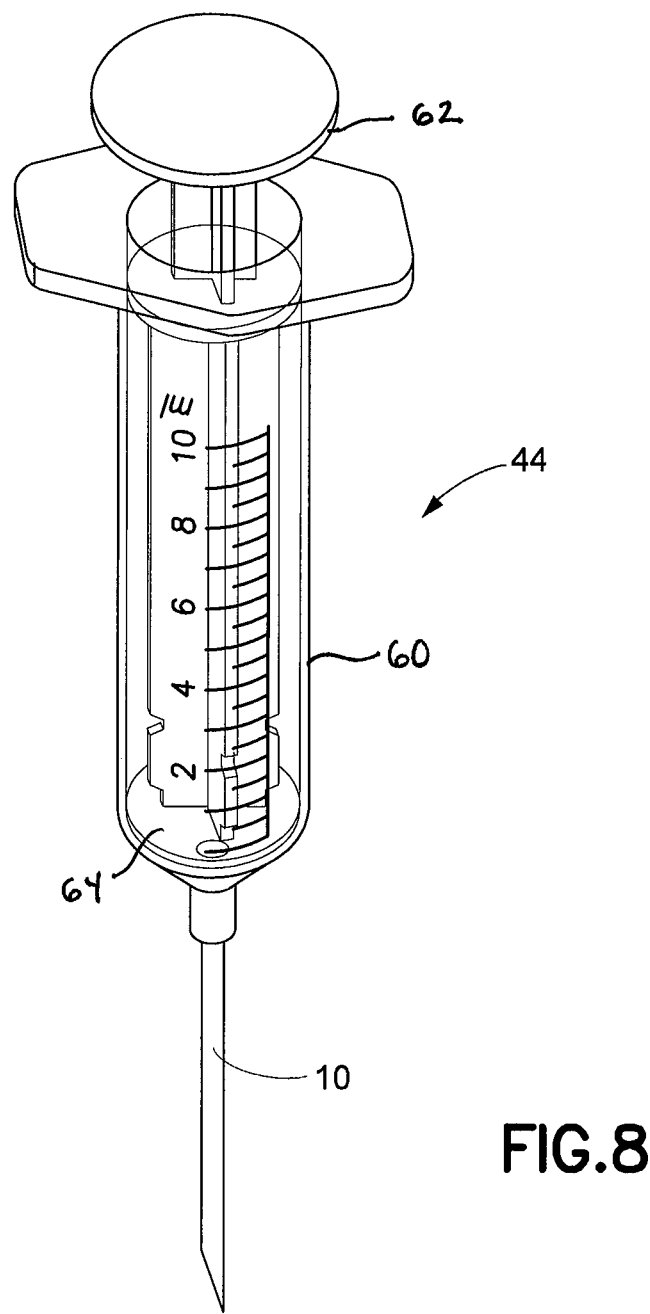
FIG. 8 is a perspective view of a syringe assembly including a multi-beveled needle according to the present invention.
Figure 9:
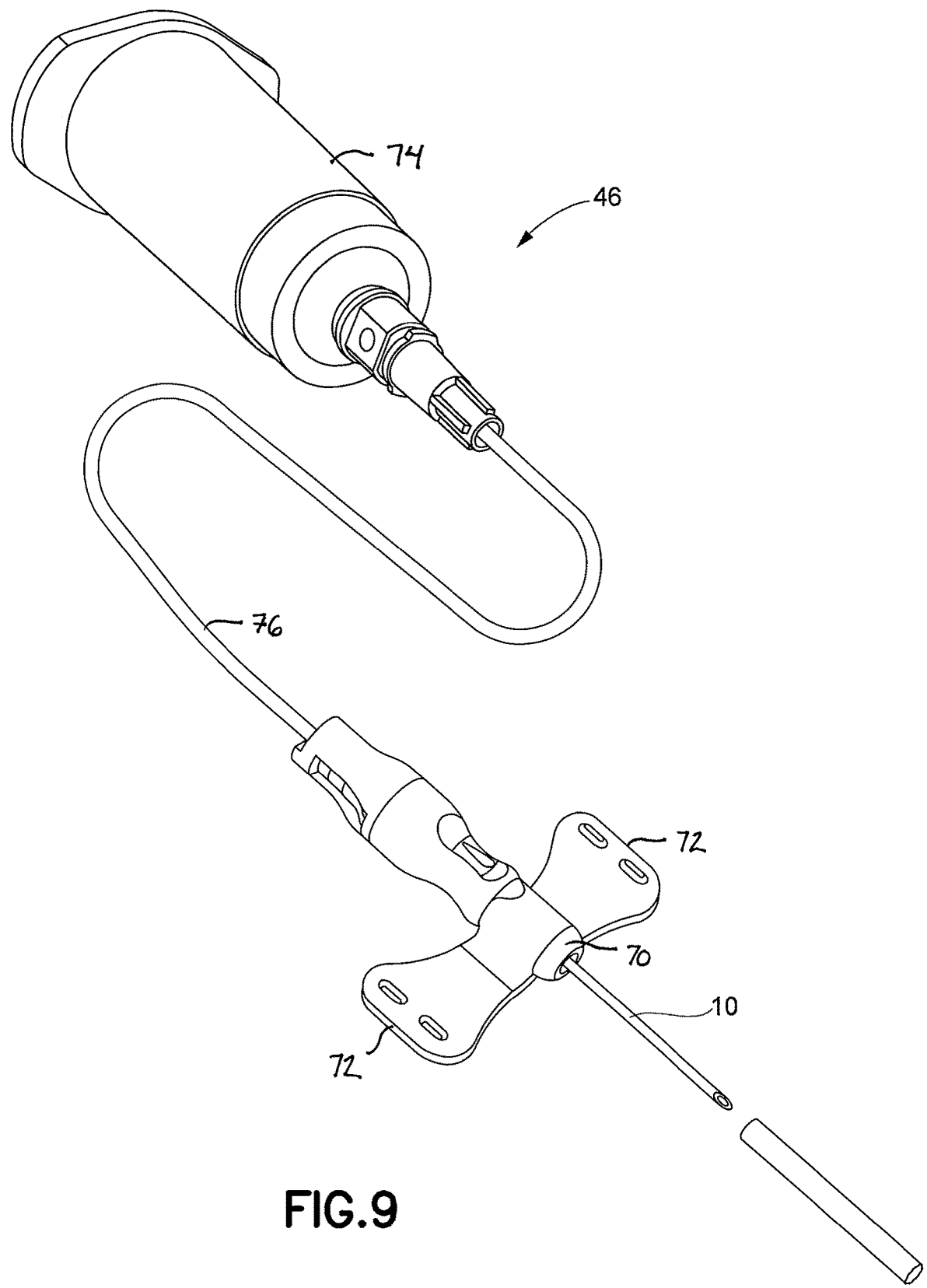
FIG. 9 is a perspective view of a blood collection assembly including a multi-beveled needle according to the present invention.

With respect to FIG. 8, the needle 10 is provided in fluid communication with the interior of the syringe barrel 60, such that transition of the plunger rod 62 having a stopper 64 connected thereto, into or out of the syringe barrel 60 expels fluid from or draws fluid into the syringe barrel 60, respectively, through the needle 10. Similarly, with respect to FIG. 9, the needle 10 is supported by a hub 70, optionally having rotatable wings 72 for easy grasping and manipulation by a user in order to assist in insertion of the needle 10 into a patient. The hub 70 may provide for fluid communication between the needle 10 and a conventional tube holder 74, such as through optional fluid line 76. The tube holder 74 is configured for receipt of a specimen collection container, such as an evacuated collection container, as is conventionally known.

The multi-beveled point 12 of needle 10 defines a fluid opening 20 for passage of fluids to and from the fluid carrying lumen 16. The needle 10 defines a lumen which extends along and about a central axis 22.

The cannula 14 may have a diameter including, but not limited to, 21 G (0.03225 in. outer diameter, 0.02025 in. inner diameter), 23 G (0.2525 in. outer diameter, 0.01325 in. inner diameter), and 25 G (0.02025 in. outer diameter, 0.01025 in. inner diameter), and a wall thickness of 0.002-0.005 inch.

As shown in FIGS. 1-4, the multi-beveled point 12 has a length "L" and has a plurality of individual bevels that together define a beveled face 24 about the periphery of the fluid opening 20. The multi-beveled point 12 has a primary bevel 26; a pair of middle bevels 28a, 28b; and a pair of tip bevels 30a, 30b. Each of the pair of middle bevels 28a, 28b and each of the pair of tip bevels 30a, 30b are substantially symmetrically formed on opposite sides of the primary bevel 26. Adjacent middle and tip bevels 28a, 30a meet at an intersect 32a demarcating the respective planes at which the middle and tip bevels 28a, 30a are formed. Adjacent middle and tip bevels 28b, 30b likewise meet at an intersect 32b. Tip bevels 30a, 30b meet at pointed tip 34 which first enters the skin of a patient or the sealing material associated with a fluid carrying vessel.

Figure 5:
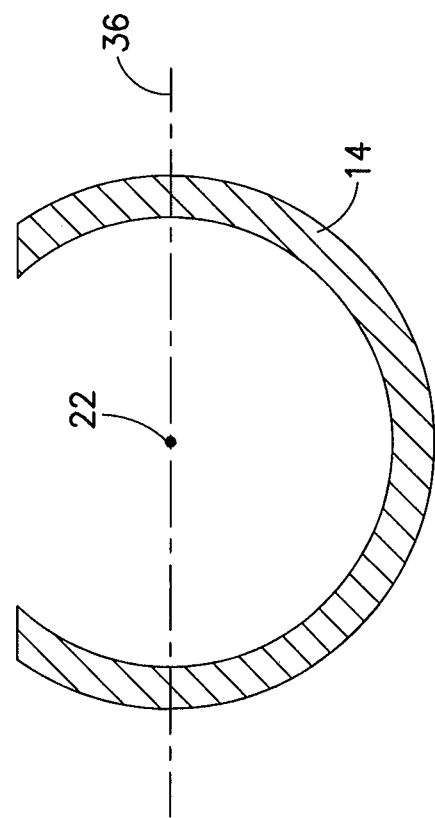
FIG. 5 is a cross-sectional view of the multi-beveled needle tip of FIG. 2 taken along line 5-5.

Primary bevel 26, middle bevels 28a, 28b, and tip bevels 30a, 30b are formed or otherwise provided on cannula 14 by inclining and/or rotating the cannula 14 through a series of angles measured relative to the central axis 22 and a reference plane 36 passing through the central axis 22. The primary bevel 26 is formed or otherwise provided on the needle 10 by inclining the central axis 22 of the needle 10 at an angle 26X measured relative to the reference plane 36 (see FIGS. 3a and 5). As shown in FIG. 1, the reference plane 36 is a plane passing through a first point 38 midway around the circumference of the cannula 14 between the center point 40 of the primary bevel 26 and the pointed tip 34 on one side of the cannula 14, a second point 42 midway around the circumference of the cannula 14 between the center point 40 of the primary bevel 26 and the pointed tip 34 on an opposing side of the cannula 14, the central axis 22 and extending in the longitudinal direction of the cannula 14. The reference plane 36 bisects the cannula 14.

Figure 6:
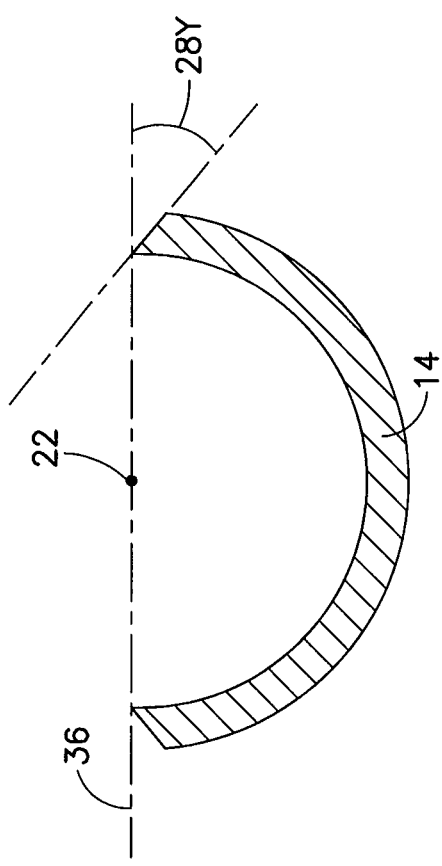
FIG. 6 is a cross-sectional view of the multi-beveled needle tip of FIG. 2 taken along line 6-6.
Figure 7:
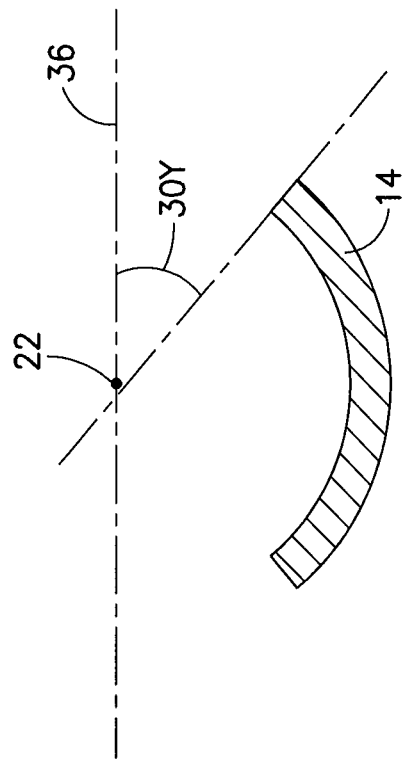
FIG. 7 is a cross-sectional view of the multi-beveled needle tip of FIG. 2 taken along line 7-7.

The middle bevels 28a, 28b and the tip bevels 30a, 30b can likewise be formed or otherwise provided on the needle 10 by inclining the central axis 22 of the needle 10 at an angle relative to the reference plane 36 as well as by rotating the needle 10 about the central axis 22 at an angle with respect to the reference plane 36. Each of the middle bevels 28a, 28b are formed or otherwise provided on the needle 10 by inclining the central axis 22 of the needle 10 at an angle 28X relative to the reference plane 36, and by rotating the needle 10 about the central axis 22 in a clockwise and a counterclockwise direction at a rotational angle 28Y relative to the reference plane 36 to form middle bevels 28a, 28b, respectively (see FIGS. 3b and 6). This provides the middle bevels 28a, 28b with outwardly directed surfaces. Similarly, the tip bevels 30a, 30b are formed or otherwise provided on the needle 10 by inclining the central axis 22 of the needle 10 at an angle of inclination 30X relative to the reference plane 36, and by rotating the needle 10 about the central axis 22 in a clockwise and a counterclockwise direction at a rotational angle 34Y (not shown) relative to the reference plane 36 to form tip bevels 30a, 30b, respectively (see FIGS. 3c and 7). This provides the tip bevels 30a, 30b with outwardly directed surfaces.

The angle of inclination 30X of the tip bevels 30a, 30b may be greater than the angle of inclination 28X of the middle bevels 28a, 28b, and the angle of inclination 28X of the middle bevels 28a, 28b may be greater than the angle of inclination 26X of the primary bevel 26. The angle of rotation 28Y of the middle bevels 28a, 28b may be equal to the angle of rotation 30Y of the tip bevels 30a, 30b, and the angle of rotation 26Y of the primary bevel 26 may be different from the angle of rotation 28Y of the middle bevels 28a, 28b and the angle of rotation 30Y of the tip bevels 30a, 30b.

The angle of inclination 26X of the primary bevel 26 may be 8°-12°, and preferably may be 10°, and the rotational angle 26Y of the primary bevel 26 may be 0°.

The angle of inclination 28X of the middle bevels 28a, 28b may be 10°-20°, 15°-20°, and preferably may be 15°, and the rotational angle 28Y of the middle bevels 28a, 28b may be 30°-50°, 36°-50°, 40°-50°, and preferably may be 40°.

The angle of inclination 30X of the tip bevels 30a, 30b may be 18-28°, 21°-28°, and preferably may be 23°, and the rotational angle 30Y of the tip bevels 30a, 30b may be 30°-50°, 36°-50°, 40°-50°, and preferably may be 40°.

When the angle of rotation 26X of the primary bevel 26 is 0° as shown in FIGS. 1-4 and 6, the surfaces of the middle bevels 28a, 28b and the tip bevels 30a, 30b are rotated outwardly from the surface of the primary bevel 26 according to their angles of rotation 28Y, 30Y as can be seen in FIGS. 3a-3c.

Inclination and rotation angles for certain needles can be selected for small diameter needles, for example 31 G and 32 G (0.00925 in. to 0.01025 in. outer diameter), which are used for injection, while the disclosed inclination and rotation angles are used with larger diameter needles, for example 21 G, 23 G, and 25 G (0.02025 in. to 0.03225 in. outer diameter), which are used for blood draw. By providing the bevels at the disclosed inclination and rotation angles for the larger diameter needles, the cumulative effect reduces the force needed to penetrate the tissue/insertion medium. The force needed to penetrate the tissue/insertion medium is especially reduced over a needle where the angle of inclination of the primary bevel 26 is equal to the angle of inclination of the middle bevels 28a, 28b. Because the needle 10 has a more gradual transition from the pointed tip 34 formed by the tip bevels 30a, 30b to the primary bevel 26, less penetration force is required to insert the needle 10 into a patient's tissue resulting in less discomfort for the patient.

The point length L from the pointed tip 34 formed by the tip bevels 30a, 30b to the most proximal portion of the primary bevel 26 may be from 0.08-0.13 inch, and the tip length l from pointed tip 34 formed by the tip bevels 30a, 30b to the intersect 32a, 32b between the middle bevels 28a, 28b and the tip bevels 30a, 30b may be from 0.02-0.04 inch.

The needle 10 in accordance with the present invention can be formed from conventional materials such as steel. Medical grade plastics, composites, ceramics, or like materials can be substituted. The needle can be lubricated with various conventional lubricants such as silicone oils to enhance the effects obtained by inventive geometry. The bevels can be formed on the needle by conventional processes such as by grinding.

The respective bevels for the multi-beveled point 12 can be formed in any order that results in a continuous beveled face 24. In one aspect, the primary bevel 26 and the middle bevels 28a, 28b can be formed before the tip bevels 30a, 30b. In another aspect, the tip bevels 30a, 30b can be formed prior to manufacturing either the middle bevels 28a, 28b or the primary bevel 26. In a further aspect, the middle bevels 28a, 28b can be formed before forming the primary bevel 26 and the tip bevels 30a, 30b. For example, the central axis 22 of the needle 10 may be inclined to the angle of inclination 26X for the formation of the primary bevel 26. The central axis 22 of the needle 10 is then inclined to an angle of inclination 30X and rotated clockwise and counterclockwise about the central axis 22 to an angle of rotation 30Y for formation of the tip bevels 30a, 30b. The central axis 22 of the needle 10 is re-inclined to an angle of inclination 28X, and rotated about the central axis 22 clockwise and counterclockwise to an angle of rotation 28Y for formation of the middle bevels 28a, 28b.

The inventive needle may be used with any suitable assembly for collecting and/or transferring blood or other fluids. Such assemblies, include, but are not limited to, a syringe assembly and a blood collection device. The syringe assembly may include a syringe barrel and the inventive needle may be attached to the syringe barrel.

Although the invention has been described in detail for the purpose of illustration based on what is currently considered to be the most practical and preferred embodiments, it is to be understood that such detail is solely for that purpose and that the invention is not limited to the disclosed embodiments but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A needle having a multi-beveled point comprising:
  a cannula having a lumen and defining a central axis therethrough and further defining a reference plane passing through the central axis and bisecting the cannula, the multi-beveled point provided at one end of the cannula,
  wherein the multi-beveled point comprises:
    a primary bevel;
    two middle bevels; and
    two tip bevels,
    wherein each of the middle bevels extends between the primary bevel and one of the tip bevels, wherein the primary bevel is provided on the cannula at a first angle of inclination and a first angle of rotation, the two middle bevels are provided on the cannula at a second angle of inclination and a second angle of rotation, and the two tip bevels are provided on the cannula at a third angle of inclination and a third angle of rotation, wherein the first angle of inclination, the second angle of inclination, and the third angle of inclination are inclined relative to the central axis, wherein the first angle of rotation, the second angle of rotation, and the third angle of rotation are each defined relative to the reference plane perpendicular to the central axis, wherein the first angle of inclination is between 8° and 12°, wherein the second angle of inclination is between 15° and 20°, wherein the third angle of inclination is greater than the second angle of inclination, wherein the second angle of rotation is equal to the third angle of rotation such that the two middle bevels and the two tip bevels comprise outwardly directed surfaces having the same angle of rotation, wherein the second angle of rotation and the third angle of rotation are each between 30° and 50°, and wherein intersects of the primary bevel and each of the middle bevels are located on one side of the reference plane, and the tip bevels are located on an opposite side of the reference plane.

2. The needle of claim 1, wherein the first angle of inclination is 10°.

3. The needle of claim 1, wherein the second angle of inclination is 15°.

4. The needle of claim 3, wherein the third angle of inclination is between 18° and 28°.

5. The needle of claim 1, wherein the third angle of inclination is between 21° and 28°.

6. The needle of claim 1, wherein the third angle of inclination is 23°.

7. The needle of claim 1, wherein the first angle of rotation is different from the second angle of rotation and the third angle of rotation.

8. The needle of claim 1, wherein the first angle of rotation is 0°.

9. The needle of claim 1, wherein the second angle of rotation and the third angle of rotation are between 36° and 50°.

10. The needle of claim 1, wherein the second angle of rotation and the third angle of rotation are between 40° and 50°.

11. The needle of claim 1, wherein a length of each of the two tip bevels is between 0.02-0.04 inches, and further wherein a total length of the multi-beveled point is between 0.08-0.13 inches.

12. A syringe assembly comprising:
a syringe barrel; and
a needle attached to the syringe barrel, the needle having a cannula having a lumen and defining a central axis therethrough and further defining a reference plane passing through the central axis and bisecting the cannula, the needle having a multi-beveled point provided at one end of the cannula,
wherein the multi-beveled point comprises:
a primary bevel;
two middle bevels; and
two tip bevels,
wherein each of the middle bevels extends between the primary bevel and one of the tip bevels,
wherein the primary bevel is provided on the cannula at a first angle of inclination and a first angle of rotation, the two middle bevels are provided on the cannula at a second angle of inclination and a second angle of rotation, and the two tip bevels are provided on the cannula at a third angle of inclination and a third angle of rotation, wherein the first angle of inclination, the second angle of inclination, and the third angle of inclination are inclined relative to the central axis, wherein the first angle of rotation, the second angle of rotation, and the third angle of rotation are each defined relative to the reference plane perpendicular to the central axis, wherein the first angle of inclination is between 8° and 12°, wherein the second angle of inclination is between 15° and 20°, wherein the third angle of inclination is greater than the second angle of inclination, wherein the second angle of rotation is equal to the third angle of rotation such that the two middle bevels and the two tip bevels comprise outwardly directed surfaces having the same angle of rotation, wherein the second angle of rotation and the third angle of rotation are each between 30° and 50°, and wherein intersects of the primary bevel and each of the middle bevels are located on one side of the reference plane, and the tip bevels are located on an opposite side of the reference plane.

13. The syringe assembly of claim 12, wherein the third angle of inclination is between 21° and 28°.

14. The syringe assembly of claim 12, wherein the first angle of rotation is different from the second angle of rotation and the third angle of rotation.

15. The syringe assembly of claim 12, wherein the first angle of rotation is 0°.

16. The syringe assembly of claim 12, wherein a length of each of the two tip bevels is between 0.02-0.04 inches, and further wherein a total length of the multi-beveled point is between 0.08-0.13 inches.

17. A blood collection device comprising:
a hub; and
a needle extending from the hub, the needle having a cannula having a lumen and defining a central axis therethrough and further defining a reference plane passing through the central axis and bisecting the cannula, the needle having a multi-beveled point provided at one end of the cannula,
wherein the multi-beveled point comprises:
a primary bevel;
two middle bevels; and
two tip bevels,
wherein each of the middle bevels extends between the primary bevel and one of the tip bevels,
wherein the primary bevel is provided on the cannula at a first angle of inclination and a first angle of rotation, the two middle bevels are provided on the cannula at a second angle of inclination and a second angle of rotation, and the two tip bevels are provided on the cannula at a third angle of inclination and a third angle of rotation, wherein the first angle of inclination, the second angle of inclination, and the third angle of inclination are inclined relative to the central axis, wherein the first angle of rotation, the second angle of rotation, and the third angle of rotation are each defined relative to the reference plane perpendicular to the central axis, wherein the first angle of inclination is between 8° and 12°, wherein the second angle of inclination is between 15° and 20°, wherein the third angle of inclination is greater than the second angle of inclination, wherein the second angle of rotation is equal to the third angle of rotation such that the two middle bevels and the two tip bevels comprise outwardly directed surfaces having the same angle of rotation, wherein the second angle of rotation and the third angle of rotation are each between 30° and 50°, and wherein intersects of the primary bevel and each of the middle bevels are located on one side of the reference plane, and the tip bevels are located on an opposite side of the reference plane.

18. The blood collection device of claim 17 further comprising a pair of wings extending transversely from the hub.

19. The blood collection device of claim 18, wherein the pair of wings is rotatable with respect to the hub.

20. The blood collection device of claim 17 further comprising a tube holder connected to the hub for receiving a collection container therein.

21. The blood collection device of claim 17, wherein the third angle of inclination is between 21° and 28°.

22. The blood collection device of claim 17, wherein the first angle of rotation is different from the second angle of rotation and the third angle of rotation.

23. The blood collection device of claim 17, wherein the first angle of rotation is 0°.

24. The blood collection device of claim 17, wherein a length of each of the two tip bevels is between 0.02-0.04 inches, and further wherein a total length of the multi-beveled point is between 0.08-0.13 inches.

* * * * *